(12) United States Patent
Qian

(10) Patent No.: US 10,370,650 B2
(45) Date of Patent: Aug. 6, 2019

(54) SYSTEM AND METHOD FOR COLLECTING A SAMPLE OF NUCLEIC ACID

(71) Applicant: Occam Biolabs, Inc., Newark, DE (US)

(72) Inventor: Mingwei Qian, Hockessin, DE (US)

(73) Assignee: Occam Biolabs, Inc., Newark, DE (US)

( * ) Notice: Subject to any disclaimer, the term of this patent is extended or adjusted under 35 U.S.C. 154(b) by 561 days.

(21) Appl. No.: 14/892,709

(22) PCT Filed: May 23, 2014

(86) PCT No.: PCT/US2014/039320
§ 371 (c)(1),
(2) Date: Nov. 20, 2015

(87) PCT Pub. No.: WO2014/190249
PCT Pub. Date: Nov. 27, 2014

(65) Prior Publication Data
US 2016/0097049 A1 Apr. 7, 2016

Related U.S. Application Data

(60) Provisional application No. 61/827,244, filed on May 24, 2013.

(51) Int. Cl.
*C12N 15/10* (2006.01)
*B65B 7/28* (2006.01)
(Continued)

(52) U.S. Cl.
CPC .......... *C12N 15/1017* (2013.01); *B01L 3/502* (2013.01); *B01L 3/508* (2013.01);
(Continued)

(58) Field of Classification Search
USPC ....................................... 422/549
See application file for complete search history.

(56) References Cited

U.S. PATENT DOCUMENTS 5,234,809 A 8/1993 Boom
5,346,994 A 9/1994 Chomczynski
(Continued)

FOREIGN PATENT DOCUMENTS

CN 102481576 5/2012
CN 202538808 U 11/2012
(Continued)

OTHER PUBLICATIONS

Extended European Search Report for European Application No. 14801362.6, dated Feb. 9, 2017, 7 pages.
(Continued)

*Primary Examiner* — Jill A Warden
*Assistant Examiner* — Brittany I Fisher
(74) *Attorney, Agent, or Firm* — RatnerPrestia

(57) ABSTRACT

A system for collecting and shipping a sample of nucleic acid, the system comprising a receptacle, a removable cap for the receptacle having a breather port and sample connection port, and a filter column removably attached to the inside of the receptacle cap in fluid communication with the sample connection port and containing a substrate for collecting the nucleic acid. A sample collection container interlocks to the sample collection port. A shipping container, closeable by a lid, is configured to detach the filter column from the receptacle cap and contain the column for shipping. Methods for collecting samples using the system preferably include a dehydrating wash step, such as with ethanol, and placement of a dessicant in the shipping container, so that nucleic acid samples can be transported under ambient, non-climate-controlled conditions, with stability for at least up to 4 weeks, ideal for collecting samples from undeveloped regions.

37 Claims, 8 Drawing Sheets

Specification includes a Sequence Listing.

(51) Int. Cl.
  *C12Q 1/6806* (2018.01)
  *B01L 3/00* (2006.01)
(52) U.S. Cl.
  CPC .............. *B65B 7/28* (2013.01); *C12Q 1/6806* (2013.01); *B01L 2200/023* (2013.01); *B01L 2200/025* (2013.01); *B01L 2200/0684* (2013.01); *B01L 2200/0689* (2013.01); *B01L 2200/185* (2013.01); *B01L 2300/042* (2013.01); *B01L 2300/046* (2013.01); *B01L 2300/048* (2013.01); *B01L 2300/0681* (2013.01); *B01L 2300/0854* (2013.01); *B01L 2300/105* (2013.01); *B01L 2400/049* (2013.01); *B01L 2400/0409* (2013.01); *B01L 2400/0605* (2013.01)

(56) References Cited

U.S. PATENT DOCUMENTS

| | | | |
|---|---|---|---|
| 6,375,855 B1* | 4/2002 | Vassarotti | B01D 61/18 210/360.1 |
| 6,720,417 B1 | 4/2004 | Walter | |
| 7,282,371 B2* | 10/2007 | Helftenbein | B01L 3/5082 435/287.2 |
| 7,862,773 B2* | 1/2011 | Ibrahim | B01L 3/508 422/402 |
| 7,897,378 B2 | 3/2011 | Block | |
| 8,158,349 B2 | 4/2012 | Block | |
| 8,216,832 B2* | 7/2012 | Battrell | B01L 3/502715 435/308.1 |
| 8,377,715 B2* | 2/2013 | Suh | B01J 20/285 422/524 |
| 8,927,261 B2 | 1/2015 | Block et al. | |
| 8,999,268 B2 | 4/2015 | Egger-Cimenti | |
| 2003/0088963 A1* | 5/2003 | Mayer | B01D 61/18 29/426.5 |
| 2005/0227269 A1* | 10/2005 | Lloyd, Jr. | B01L 3/50825 435/6.18 |
| 2007/0092403 A1* | 4/2007 | Wirbisky | C12N 1/06 422/65 |
| 2007/0202538 A1* | 8/2007 | Glezer | B01L 3/5025 435/7.1 |
| 2008/0017577 A1* | 1/2008 | Yi | B01L 3/502 210/645 |
| 2009/0246877 A1* | 10/2009 | Moran, Jr. | B01L 3/5021 436/43 |
| 2010/0200509 A1 | 8/2010 | Suh | |
| 2010/0274155 A1 | 10/2010 | Battrell et al. | |
| 2011/0056893 A1 | 3/2011 | Leach | |
| 2012/0225001 A1* | 9/2012 | Koeda | B01L 7/525 422/560 |
| 2012/0291872 A1* | 11/2012 | Brady | G01N 35/1065 137/3 |
| 2013/0037509 A1 | 2/2013 | Rahimy | |
| 2014/0011229 A1 | 1/2014 | Nakatsuka | |
| 2014/0147851 A1 | 5/2014 | Qian | |
| 2017/0335313 A1 | 11/2017 | Qian | |

FOREIGN PATENT DOCUMENTS

| | | |
|---|---|---|
| CN | 102811693 | 12/2012 |
| JP | H03123837 A | 5/1991 |
| JP | 1996508395 A | 2/1994 |
| JP | H07103869 A | 4/1995 |
| JP | 2001511644 A | 8/2001 |
| JP | 2007529210 A | 10/2007 |
| RU | 2244559 C2 | 1/2005 |
| WO | 9403103 A1 | 2/1994 |
| WO | 2004011122 | 2/2004 |
| WO | 2005090567 A1 | 9/2005 |
| WO | 2005102526 A1 | 11/2005 |
| WO | 2010101865 | 9/2010 |
| WO | 2012135815 | 10/2012 |
| WO | 2013003309 A1 | 1/2013 |
| WO | 2013114220 A2 | 8/2013 |

OTHER PUBLICATIONS

International Search Report and Written Opinion of the International Searching Authority for International Application No. PCT/US15/61917 dated Feb. 5, 2016.
Russian Official Action for Russian Application No. 2015155282/10(085250), dated Oct. 10, 2017 with translation14 pages.
Notice of Reasons for Rejection for Japanese Application No. 2016-515112, dated Apr. 3, 2018, including English translation, 4 pages.
Chinese Office Action for Chinese Application No. 201480042043.4, including English translation, 18 pages.
International Preliminary Report on Patentability for International Application No. PCT/US2015/061917, dated Jun. 1, 2017, 8 pages.
Extended European Search Report for European Application No. 15 860 729.1, dated May 24, 2018, 7 pages.
International Preliminary Report on Patentability (Chapter I of the Patent Cooperation Treaty) for International Application No. PCT/US14/039320 dated Nov. 24, 2015.
International Search Report for International Application No. PCT/US14/39320 dated Oct. 22, 2014.
QIAamp Circulating Nucleic Acid Handbook, Second Edition, Jan. 2011, pp. 1-56.
Written Opinion of the International Searching Authority for International Application No. PCT/US14/39320 dated Oct. 22, 2014.
Second Chinese Office Action for Chinese Application No. 201480042043.4, dated Sep. 1, 2017, including English translation, 13 pages.

* cited by examiner

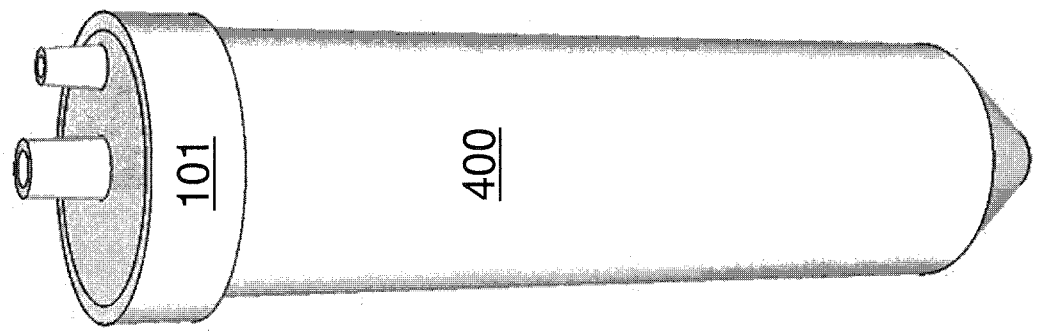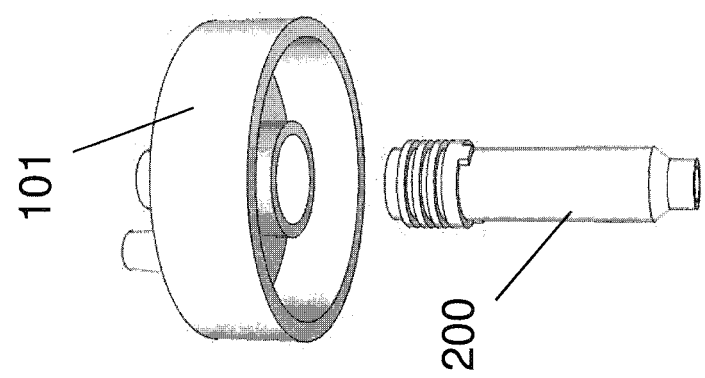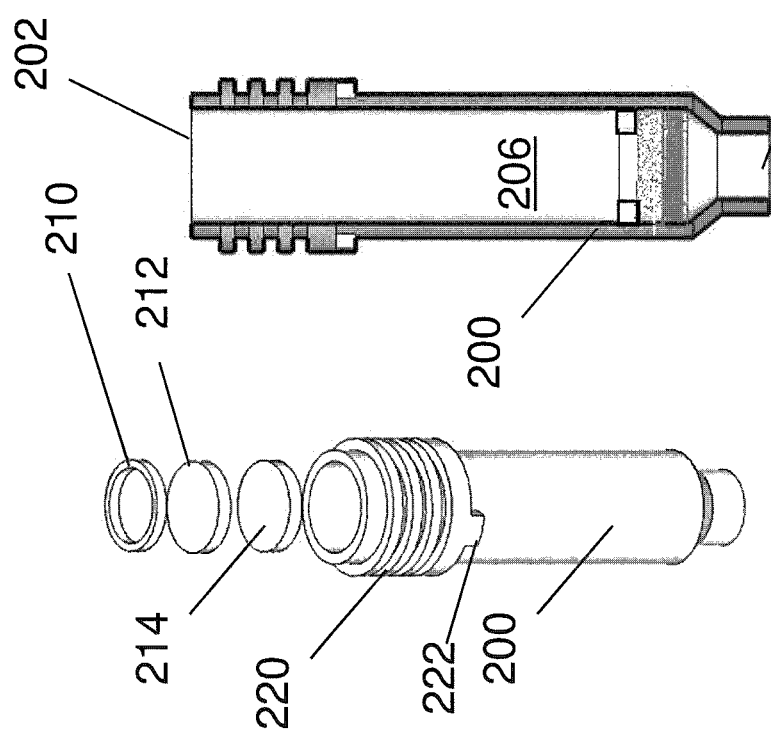

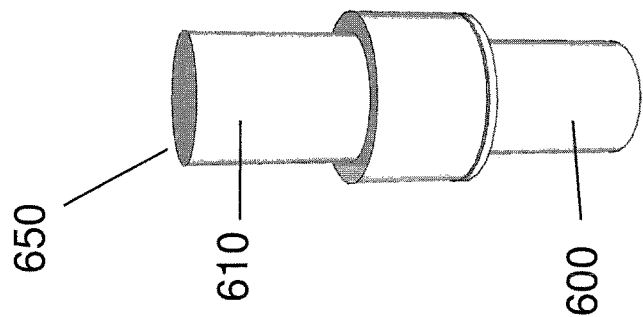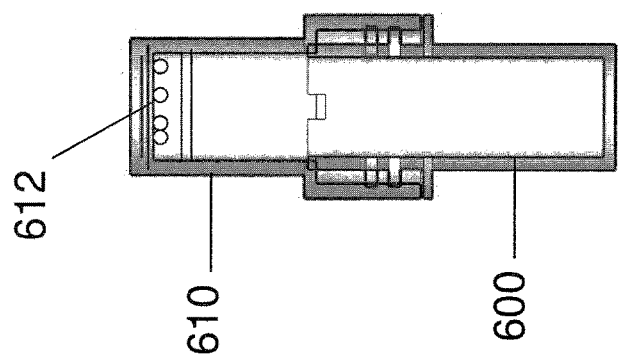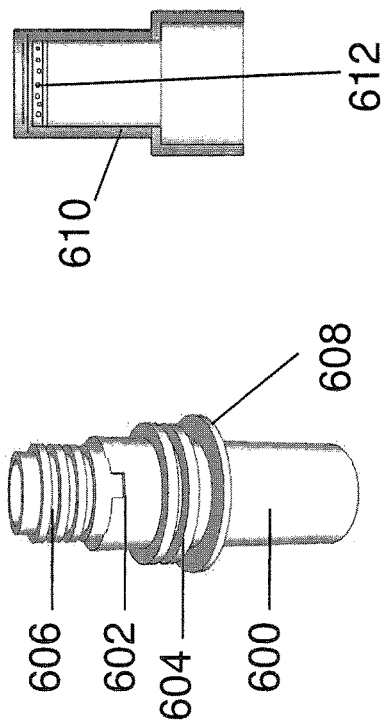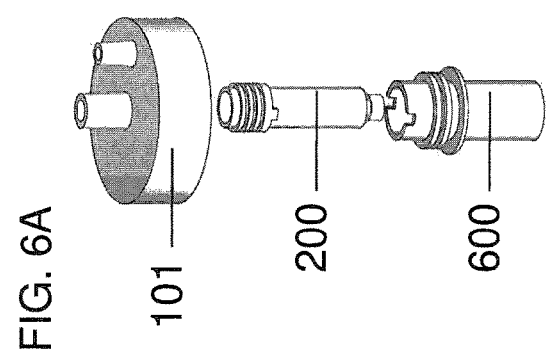

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccttggtcct tctcgggctg                                                    20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttccatcttc tggtgggtgt c                                                  21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cttcgtggcc ttggtccttc                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ttctggtggg tgtcttgagt                                                    20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
cttcgtggcc ttggtccttc tc                                                 22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gatggaaccc atacacatag ca                                                 22

<210> SEQ ID NO 7
<211> LENGTH: 23
<212> TYPE: DNA
<213> ORGANISM: Artificial Sequence -continued

```
<220> FEATURE:
<223> OTHER INFORMATION: Primer

<400> SEQUENCE: 7
cgagtgaaac acgttacttt gga                                              23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gatggtgctg cttacaggtc tc                                               22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
tcccagaagt aacacagggc a                                                21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gtaggataag gcctgaggat ag                                               22

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
ggtcagcacg attcggag                                                    18

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gccaacacca agtagacgg                                                   19

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
cgcgctactc tctctttctg g                                                21
```

```
<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
agtcaacttc aatgtcggat gg                                              22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ccaacacaaa tggttcccag                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgagttgtcc acagtcagca                                                 20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gcctacgaca aacagaccta aa                                              22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ttgaagagta tgcaatgagc ga                                              22
```

SYSTEM AND METHOD FOR COLLECTING A SAMPLE OF NUCLEIC ACID

CROSS REFERENCE TO RELATED APPLICATIONS

This application is a U.S. National Phase Application of PCT International Application PCT/US2014/039320, filed May 23, 2014, which claims priority to U.S. Provisional Patent Application No. 61/827,244, filed May 24, 2013, the contents of which are incorporated herein by reference.

BACKGROUND OF THE INVENTION

Current systems and methods for collection, extraction, and detection of nucleic acid from biological samples for testing are typically complicated, requiring multiple steps with technically trained personnel, and not optimized for processing samples with large volumes or for preventing cross-contamination in sample processing and stabilization for shipment.

A variety of body fluids, such as blood, plasma, serum, Cerebrospinal fluid (CSF), pleural effusion, ascites, urine etc., contain short chain nucleic acid (NA) fragments, namely, cell-free nucleic acids (cfNA), or circulating nucleic acids (cNA). Altered nucleic acids, originated endogenously from a tumor, or "exogenously" from fetus or pathogenic infection inside the body, may present as cfNA in the peripheral blood at very low concentrations and may be detectable, and further, be distinguishable from normal host cfNA. Extraction of sufficient amount of those cfNA from plasma or serum for testing requires processing a relatively large volume of fluid, which imposes a unavoidable technical challenge in clinical diagnostic settings. Accordingly, there is a need the field for new methods to meet such challenges.

Exemplary such methods for detecting, for example, tuberculosis, are described in Pending PCT published application WO2012135815, invented by the inventor of this application, and incorporated herein by reference. Such testing, however, may be most useful in regions of the world lacking ready access to the expensive processing equipment used in analysis of the samples. Accordingly, there is a need in the art for a collection system and methodology that will permit capturing nucleic acid in sufficient amounts from large volume biological samples, to run later analysis, to prevent contamination from the environment and operators, and to preserve and ship the nucleic acid, so that nucleic acid can be collected at a point of care facility using relatively inexpensive equipment, and then shipped in a stabilized form to a central location for further processing and assays.

Various methods of extraction suitable for isolating circulating DNA or RNA from large volumes of biological fluids are known, such as those described, for example, in QIAamp® Circulating Nucleic Acid Handbook, ($2^{nd}$ edition, 02, 2011, Qiagen), and an improved spin column extraction method described in U.S. Pat. No. 5,234,809 (Boom technology). U.S. Pat. No. 5,346,994 describes a technology an organic liquid extraction method using phenol-chloroform. Both of these methods may be used for large volume extraction, such as from plasma or serum specimens, but the organic reagents are toxic, which limits its use.

U.S. Pat. Nos. 7,897,378 and 8,158,349 describe devices and method for purifying or isolating nucleic acids from larger sample volumes, including systems comprising a pair of cooperating hollow bodies through which samples are passed into a collection vessel, with nucleic acids bound to a binding material in one of the hollow bodies. The hollow body containing the retained sample is transferred to a first receiving vessel for washing, then the purified or isolated nucleic acids are eluted and collected in a second receiving vessel for further analysis.

U.S. Pat. No. 5,234,809 (Boom), for example, incorporated herein by reference, discloses a method for isolating nucleic acids, which is suitable for a multiplicity of different uses. It describes a method for isolating nucleic acids from nucleic acid-containing starting materials by incubating said starting material with a chaotropic buffer and a DNA-binding solid phase. The chaotropic buffers effect, if necessary, both lysis of the starting material and binding of the nucleic acids to the solid phase.

SUMMARY OF THE INVENTION

One aspect of the invention relates to a method and a system for processing a biological sample. Processing as referred to herein comprises lysing, binding, washing, stabilizing and eluting biomolecules of the biological sample.

One embodiment comprises system for collecting a sample of nucleic acid, the system comprising a receptacle defining an internal volume, a removable cap for the receptacle and having a connection interface in fluid communication with a sample connection port in the cap, a filter column adapted to be removably attached to the connection interface of the receptacle cap, a sample collection container, and a shipping container. The removable cap for the receptacle has an internal side facing the internal volume of the receptacle and an external side facing away from the internal volume. The cap has a breather port communicating between the internal side and the external side and a sample connection port communicating between the internal side and the external side. The sample connection port has a first interlocking component for releasably locking the sample connection port to a cooperating second interlocking component. The connection interface in fluid communication with the sample connection port is located on the internal side of the cap. The filter column has an open first end, an open second end, and an internal passage therebetween containing a substrate for collecting the nucleic acid. The sample collection container comprises a second interlocking component adapted to connect to the first interlocking component of the sample collection port in the receptacle cap. The shipping container has an open end and defines a volume adapted to contain the filter column. The shipping container is adapted to releasably engage the filter column for detaching it from the connection interface of the receptacle cap. The shipping container further comprises a removable lid for temporarily sealing the filter column within the shipping container. The shipping container contains a desiccant in some embodiments.

The filter column substrate may comprises a filter, a supporting frit downstream of the filter, and a retaining ring upstream of the filter. The sample connection port interlocking components may comprise a Luer lock fitting. In some embodiments, the system may further comprise a vacuum chamber having an internal portion adapted to be connected to a source of vacuum and an external portion having one or more wells, each well adapted to receive one of the receptacles, with one or more vacuum connection ports in communication with the internal portion of the chamber and adapted to be connected to the breather port of the receptacle via a flexible conduit.

In some embodiments, the filter column and the receptacle cap are functionally connected by a threaded interface.

The filter column may have a first member, such as a first tab, disposed on an external surface thereof adapted to be releasably engaged by a cooperating second member, such as a second tab, disposed on an internal surface of the shipping container, such that the second member transmits force to the first member when a torsional force is applied to the filter column in a direction for unscrewing the filter column from its threaded connection with the receptacle cap.

The system may further comprise a three-way port having a first port adapted to be disposed to the receptacle cap sample connection port, a second port adapted to be connected to the collection container, and a third port adapted to be connected to a fluid source containing a fluid for treating the sample after it has been collected. One or more containers of fluid, such as a washing fluid, such as ethanol, may be connected to the third port.

The collection container may comprise a syringe and the three way port may comprise a check valve adapted to exclusively permit flow from the collection container into the receptacle when a positive relative pressure exists between the sample collection container and the receptacle, and to exclusively permit flow from the fluid source into the collection container when a negative relative pressure exists between the sample collection container and the fluid source.

Another aspect of the invention comprises a sterile removable cap for a receptacle, the cap having an internal side for facing the internal volume of the receptacle and an external side opposite the internal side, the cap comprising a breather port communicating between the internal side and the external side and a sample connection port communicating between the internal side and the external side, the sample connection port comprising a first interlocking component for releasably locking the sample connection port to cooperating second interlocking component, the internal side of the cap comprising a connection interface in fluid communication with the sample connection port. A sterile filter column may be removably attached to the connection interface of the receptacle cap, the filter column having an open first end, an open second end, and an internal passage therebetween containing a substrate for collecting the nucleic acid.

Still another aspect of the invention comprises a method for collecting a sample of nucleic acid, the method comprising the steps of: (a) providing the collection system described herein; (b) collecting a volume of sample-containing fluid in the sample collection container; (c) connecting the sample collection container to the receptacle via the sample collection port; (d) passing the volume of sample-containing fluid from the sample collection container through the filter column, thereby collecting the sample on the substrate and collecting a reminder in the receptacle; (e) placing the shipping container open end over the filter column, engaging the filter column with the shipping container, and detaching the filter column from the receptacle cap; and (f) temporarily sealing the shipping container with the removable lid. The sample-containing fluid may comprise, for example, a lysate comprising an extract of bodily fluid collected from a patient. Where the sample collection container comprises a syringe, the step of passing the volume through the filter column may comprise manually applying pressure to a plunger of the syringe in one embodiment, or attaching the breather port of the receptacle cap to a source of vacuum, and then applying a negative pressure across the filter column using the vacuum source, in another embodiment.

In certain embodiments, the sample collected on the substrate may be further treated after step (d) by passing one or more volumes of fluid, such as a dehydrating washing fluid such as ethanol, through the filter column before performing step (e). Additionally, a desiccant may be provided in the shipping container. A sample dehydrated and kept dry with a desiccant may be transported under ambient, non-climate-controlled conditions and may be stable for up to 4 weeks before further processing after completion of step (f). Such a method may be particularly useful for processing the collected nucleic acid at minimally-equipped medical-care settings, such as small, remote and/or peripheral clinics, and shipping the collected samples to a better-equipped central laboratory for further analysis of the collected samples for detection of a disease, such as for detection of latent tuberculosis.

BRIEF DESCRIPTION OF THE DRAWINGS

FIG. 2A depicts an exemplary filter column for attachment to the exemplary receptacle cap of FIG. 1.

FIG. 2B depicts a cross section of the exemplary filter column of FIG. 2A

FIG. 3 is an exploded view of the filter column of FIG. 2A and the receptacle cap of FIG. 1 showing how they interface with one another.

FIG. 4 depicts the receptacle cap of FIG. 1A attached to an exemplary receptacle.

FIG. 6A depicts an exemplary shipping container bottom portion.

FIG. 6B illustrates how the exemplary shipping container of FIG. 6A fits over the exemplary filter column for unscrewing it from exemplary receptacle cap 1A.

FIG. 6C is a cross sectional drawing of an exemplary shipping container top portion.

FIG. 6D is a cross sectional drawing of the exemplary shipping container bottom portion of 6A sealed by the exemplary shipping container top portion of FIG. 6C.

FIG. 6E is a perspective view of the sealed shipping container of FIG. 6D.

DETAILED DESCRIPTION OF THE INVENTION

Figure 1A:
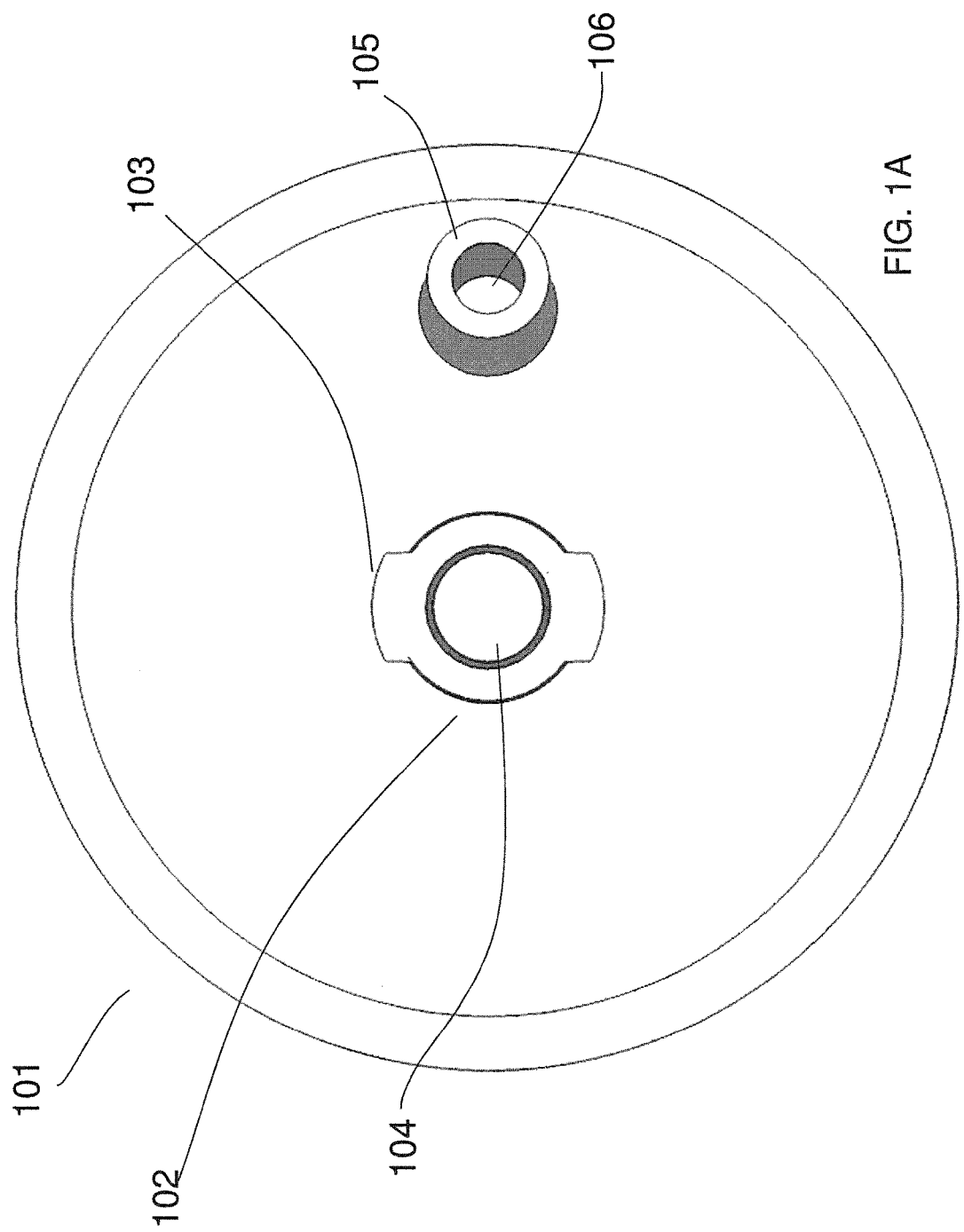
FIG. 1A depicts a plan view of an exemplary receptacle cap embodiment according to one aspect of the invention.
Figure 1B:
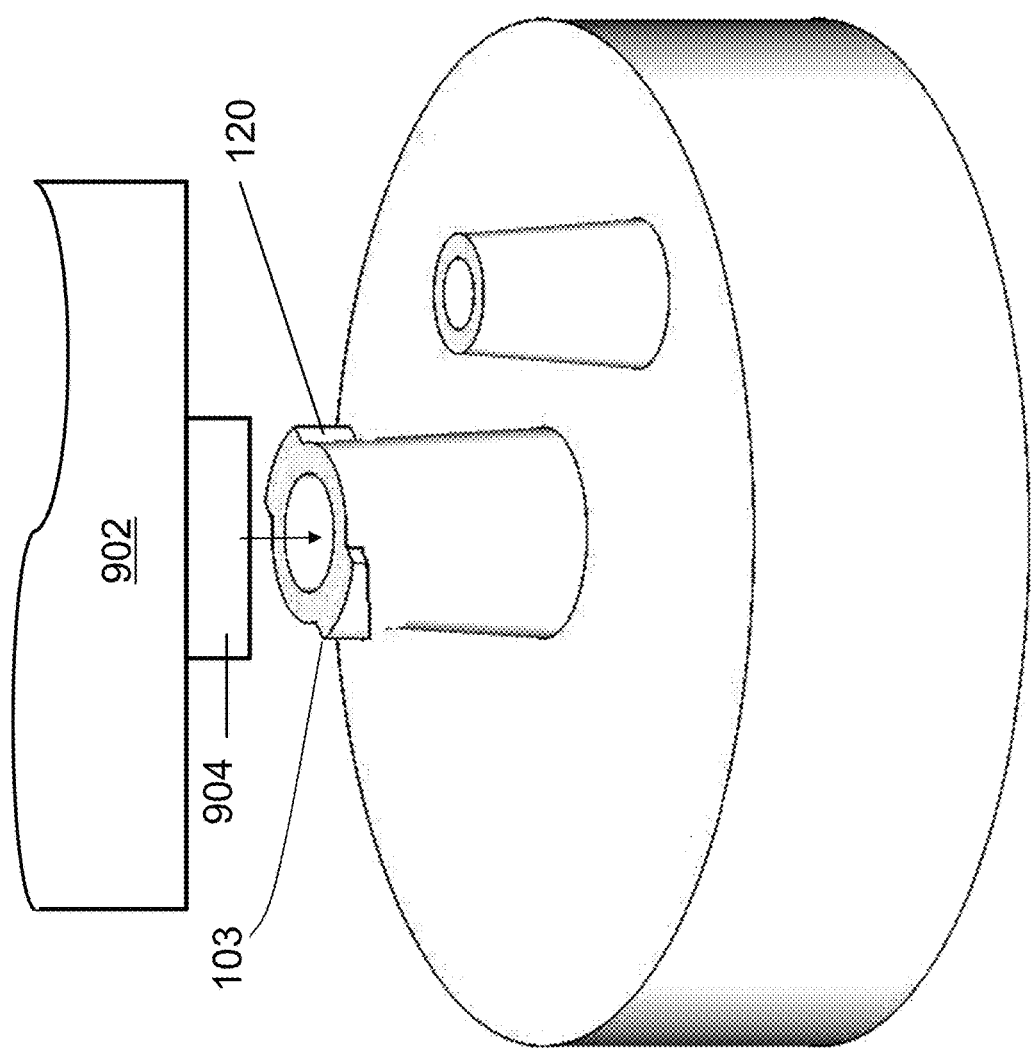
FIG. 1B depicts a perspective side view of the exemplary receptacle cap of FIG. 1A.

One aspect of the invention is a system for collecting a sample of nucleic acid. The exemplary system comprises a receptacle, such as receptacle 400 of FIG. 4, which defines an internal volume. Although shown with an exemplary geometry, the invention is not limited to any particular size and shape of the receptacle. The receptacle has a removable cap 101, such as the exemplary embodiment depicted in FIGS. 1A-1C, having an internal side 107 facing the internal volume of the receptacle and an external side 102 facing away from the internal volume. FIG. 1A shows the external side of the cap. The cap has a breather port 105, such as a male Luer slip connection, communicating between the internal side and the external side through passageway 106, and a sample connection port 103 communicating between the internal side and the external side, through passageway 104. The sample connection port comprises a first interlocking component, such as a Luer lock connection 120, for releasably locking the sample connection port to a cooperating second interlocking component 904 of a sample transfer container 902, also referred to herein as a sample collection container, such as a syringe. Both ports 120 and 105 can be easily opened or closed by Luer-fitting caps or plugs (not shown). When downward pressure is applied to the plunger of a syringe connected to port 120 to force liquid movement, port 105 is opened to allow displaced air to exit receptacle 400. When vacuum is used to force liquid movement from a connected source (which may still be a syringe), port 105 is connected to a vacuum source. The internal side of the cap comprises a connection interface 108 in fluid communication with the sample connection port 103. The cap may be threaded with female threads 110 for being screwed onto a receptacle having male threads (not shown), although any functional connection between the cap and the receptacle may be utilized.

Figure 1C:
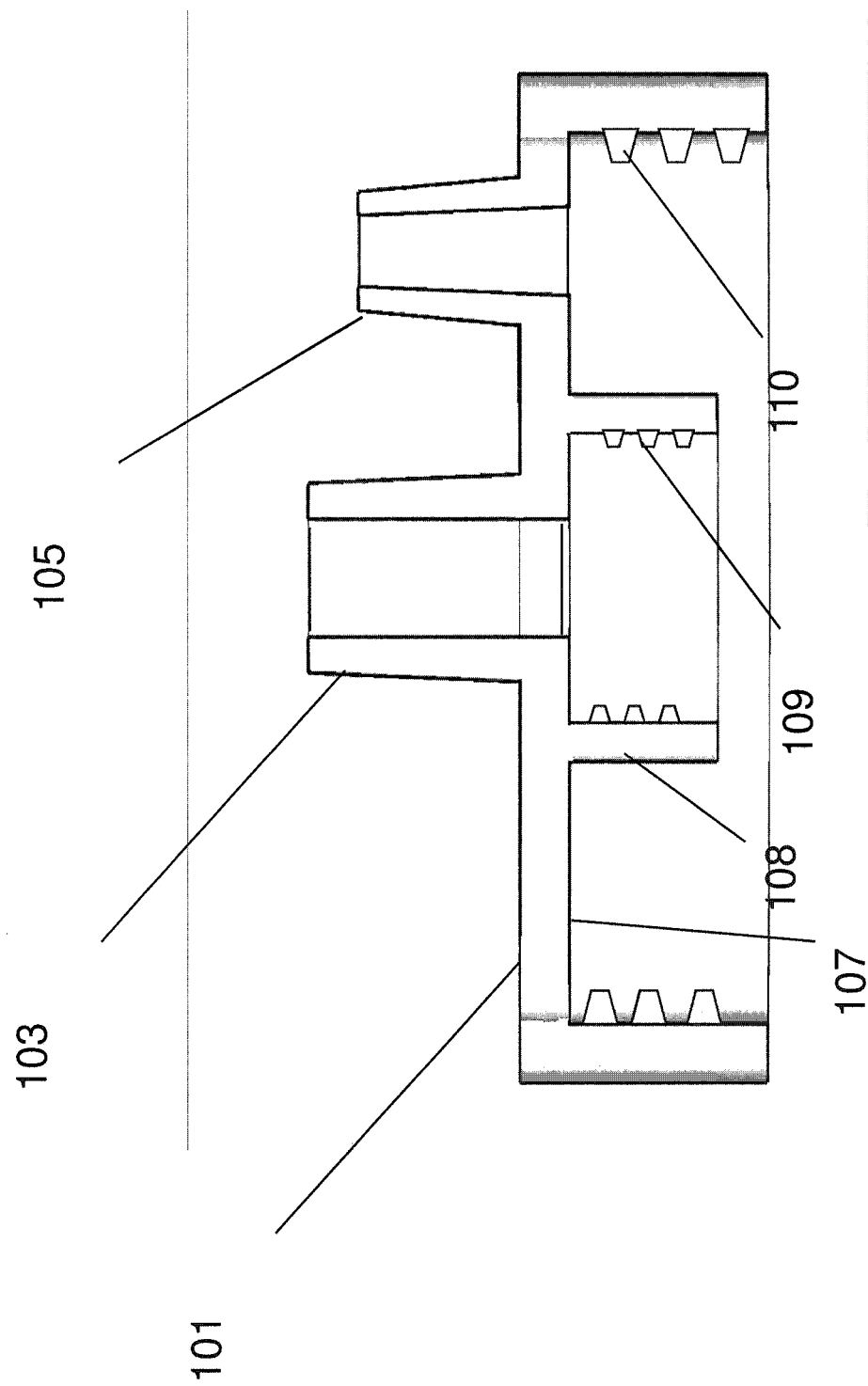
FIG. 1C depicts a cross-sectional view of the exemplary receptacle cap of FIG. 1A.

A filter column with a solid phase extraction matrix inside, such as a silica gel membrane, sintered porous glass frit, or glass fiber filter paper, such as the exemplary filter column 200 depicted in FIGS. 2A and 2B, is adapted to be removably attached to the connection interface of the receptacle cap. For example, as shown in FIG. 1C, the connection interface 108 may have female threads 109 that mate with male threads 220 on filter column 200. The filter column has open ends 202 and 204 and an internal passage 206 there between containing a substrate 212 for collecting the nucleic acid. The filter column may also be referred to as a "hollow body" because it is designed for fluid to pass through it without the fluid being retained therein in the way that fluid is retained in a vessel or a receptacle. The filter column substrate 212 may be adjacent a porous frit 214, and a retaining ring 210 may create a frictional engagement against the inside of the column to retain the substrate and frit in a position adjacent the neck of the filter column.

Substrate 212 may comprise a column binding matrix comprising a solid matrix which allows fluid to pass through the matrix. In certain aspects the matrix is highly porous so as to maximize surface area exposed to buffer solutions and thereby maximize the binding capacity of the matrix. A matrix can be made of various materials. In certain specific embodiments, the binding matrix may be a silica material (formed primarily of SiO2) such as glass fiber, silica beads, silica gel, sintered porous glass frit, etc. Numerous commercial providers of silica matrix are known, such as, for example, type GF/A, GF/B, GF/C, GF/D and GF/F glass fiber filters produced by Whatman (NJ). Such filters are of particularly known for use in the purification of nucleic acid molecules. In other embodiments, a variety of solid matrices, such as ion exchange, affinity and surface modified matrices suitable for certain biomolecule extraction and separation may be applied. The binding matrix may be any material in which particles or fibers of the nucleic acid binding material may be embedded. The matrix material is generally permeable to liquids so that the sample can pass through the matrix, the nucleic acids make contact with and bind to the nucleic acid-binding material, and other components of the sample can leave the matrix. The binding matrix may comprise any support material known in the art, including materials selected from the group consisting of siliceous materials, silica gel, glass, Zeolite, aluminum oxide, titanium dioxide, Zirconium dioxide, kaolin, gelatinous silica, magnetic particles, a sintered porous glass frit, and ceramics or polymeric support materials. The nucleic acid-binding material may be any material to which nucleic acids bind (typically non-covalently) under certain conditions whereas other substances in a sample do not bind under these conditions. Nucleic acid binding is typically reversible such that the nucleic acids can be subsequently eluted again from the material by changing the conditions.

In one embodiment, column 200 may be similar in geometry to a Mobicol column, available from Boca Scientific (FL), or may be a specially modified or specially manufactured version thereof. A design with such a geometry can be centrifuged in a microcentrifuge and permits samples with large volume to be processed easily with a syringe. The porous frit 214 may comprise inert plastic with a pore size 10-90 μm. The solid extraction matrix (substrate) may comprise GF/D filter paper (Whatman, N.J.), such as made by punching the filter paper into disks that fit within the inside diameter of the column. Two or more layers of the filter disks may be put on top of the frit. A back-up ring (Ring-Store, WA), such as a ring made of PTFE (such as Teflon®) or plastic such as polyethylene (PE) or polypropylene (PP), may be put on the top of the filter disks (as seen in FIG. 2A) to prevent the filter disks moving.

An opener and shipping container, such as exemplary container 650 depicted in a fully assembled configuration in FIG. 6E, comprises a bottom portion 600 and mating top portion 610. The cooperating bottom portion and top portion define a volume adapted to contain the filter column for shipping. The bottom portion 600 of the shipping container has an open top and is adapted to releasably engage the filter column for detaching it from the connection interface of the receptacle cap. For example, the filter column may have a tab 222 shown in FIG. 2A that is engaged by notch 602 of FIG. 6A. The enclosed shipping container is sealed from the environment to prevent contamination and moisture which may cause accelerated degradation (hydrolysis) of nucleic acid, in particular RNA. The enclosed shipping container may further comprise a pre-packaged desiccant that induces or sustains a state of dryness (desiccation), such as granular or beaded form of silica gel, therein, such as desiccant 612 depicted in the upper portion of the container in FIGS. 6C and 6D. The desiccant location could also be in a lower portion of the container and is not limited to any specific location or configuration. The desiccant may comprise any suitable material known in the art for providing and sustaining desiccation, such as but not limited to, montmorillonite clay, lithium chloride, activated alumina, alkali alumino-silicate, DQ11 Briquettes, silica gel, molecular sieve, calcium sulfate, or calcium oxide. The desiccant may contain a moisture indicator that gradually changes its color when it transitions from an anhydrous (dry) to a hydrated (wet) state, such as is known for some silica gels.

Although shown with the sample connection port protruding from the external side of the cap with a Luer lock fitting, the invention is not limited to any particular type of interlocking connection, nor to any particular configuration of the sample connection port. While some type of locking engagement between the sample connection port and the sample container is preferred, any type of reversibly locking engagement may be provided. The sample transfer container is not shown, but may be a standard syringe with a cooperating Luer lock fitting. In an exemplary method, therefore, the syringe is interlocked with the receptacle cap, and the syringe plunger is depressed to force a solution containing nucleic acid, in the presence of binding reagents such as chaotropic reagents and alcohol, to be passed through the filter column. The nucleic acid is thus retained on the filter 212, while the filtrate passes into the receptacle 400. As noted above, the syringe plunger may be depressed manually with port 105 open, or a vacuum source may be attached to port 105 such that the vacuum causes the syringe plunger to be depressed as the solution empties from the syringe.

Chaotropic reagents are well known in the art as substances that change the secondary, tertiary and/or quaternary structure of proteins or nucleic acids but do not affect at least their primary structure. Examples are guanidinium thiocyanate, guanidinium hydrochloride, NaI, KI, sodium thiocyanate or combinations of these substances. Chaotropic reagents disturb the ordered structure of liquid water and cause DNA or RNA to bind from this aqueous solution to a glass surface. Under some conditions, inclusion of alcohol, such as ethanol or isopropyl alcohol, facilitates NA binding to the surface. Substances such as NaCl, KCl or CaCl2 may be present in the solution in order to modify the ionic strength. The property of DNA and RNA to bind under chaotropic conditions to glass surfaces is used to isolate them from a solution containing other biological materials. Binding to the glass surface is reversible, as, for example, if the concentration of the chaotropic reagents is reduced or the chaotropic reagents are entirely removed, the DNA or RNA can be eluted again.

Figure 5:
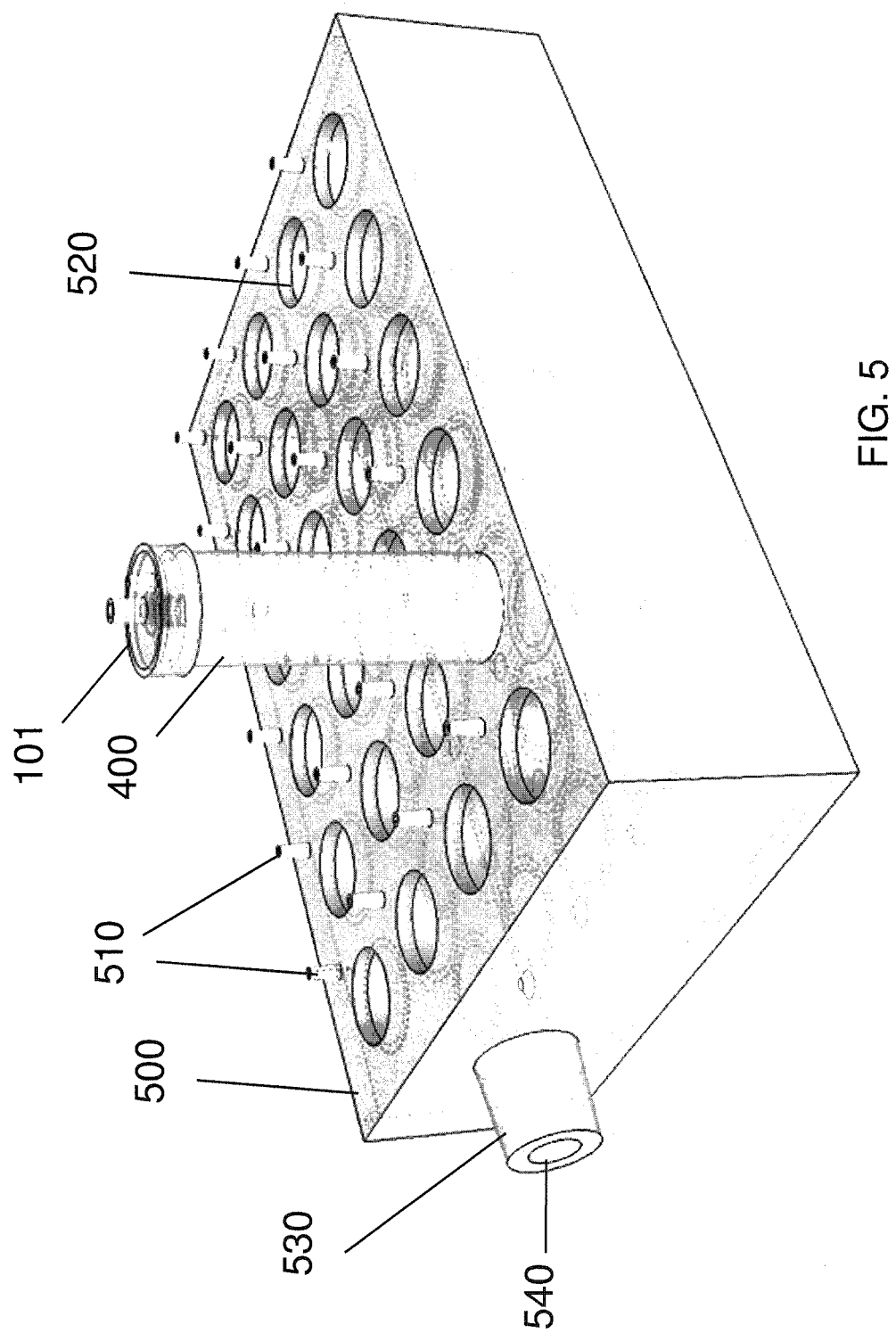
FIG. 5 depicts an exemplary vacuum chamber design for holding a plurality of the exemplary receptacles of FIG. 4.

Thus, the collection system may further comprise a vacuum chamber 500 such as depicted in FIG. 5. The vacuum chamber is adapted to be connected to a source of vacuum, such as via connection port 530, which is in communication with the inner volume of the vacuum chamber via passageway 540. The outside of the vacuum chamber 500 has a plurality of wells 520, each well adapted to receive one of the receptacles 400. A plurality of vacuum connection ports 510 are in communication with the internal portion of the chamber and adapted to be connected to the breather port 105 of the receptacle cap 101 via a flexible conduit (not shown). Thus, for example, the plurality of wells can be filled with receptacles, each receptacle cap connected to one of the vacuum ports 510, and the vacuum thus causes the sample containing fluid in a plurality of sample transfer containers to be filtered through a plurality of filter columns into a plurality of receptacles. Although shown with a plurality of wells in the vacuum chamber, the vacuum chamber may have only a single well, or greater or fewer wells than are depicted. The vacuum ports on the vacuum chamber may have removable caps or valves so that the chamber may be used with fewer than all of the vacuum ports connected to receptacles in the receptacle wells.

Figure 7B:
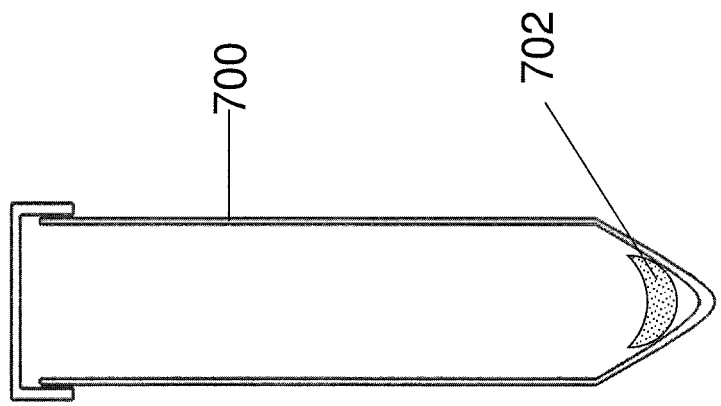
FIG. 7B depicts the lysing container of 7A containing lysis solution in dried form.
Figure 7A:
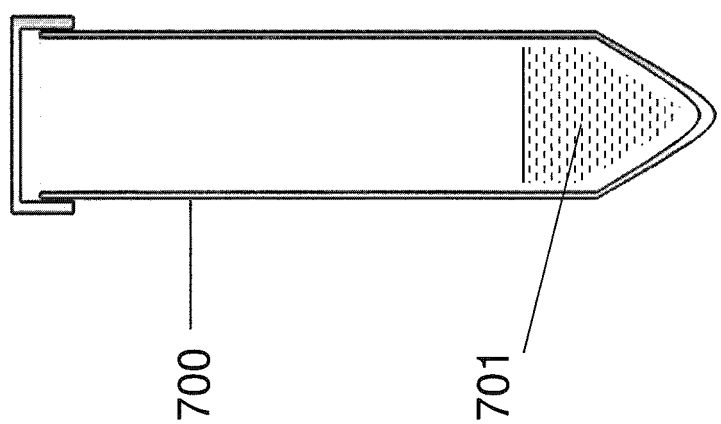
FIG. 7A depicts a lysing container containing lysis solution in aqueous form.

The collection system may further comprise a lysing container (FIGS. 7A and 7B) containing pre-formulated lysis reagents, and a first syringe to transfer the liquid specimen (serum, plasma) into the lysing container, and a second syringe to transfer the lysate into the extraction device. Each syringe preferably comprises a metal or plastic needle that is safe (blunt), is long enough to reach the bottom of the relevant container from which the syringe is used to extract fluid, and has an internal diameter (ID) large enough to permit relatively fast liquid flow. The lysis reagents may comprise, for example, at least: a nonionic detergent such as Triton X-100 or BJ58, or a combination of the nonionic detergent with an anionic detergent, such as sodium lauroyl sarcosinate, a protease such as proteinase K, a salt or chaotropic agent, such as Lithium chloride, guanidine, guanidine thoicyanate, urea, a reducing agent such as Dithiothreitol (DTT), a chelator such as ethylene diamine tetraacetic acid (EDTA), and a buffer such as tris(hydroxymethyl)aminomethane (Tris). It is well-known guanidine and guanidine thiocyanate have strong DNase and RNase inhibitory activity at molar concentration. The lysing reagents may in a solution, or in a dried form (dehydrated), for example, by lyophilization (freeze-drying) or spray-coating within the lysing container.

The specimens, in the forms of aqueous fluids, such as blood, plasma. serum, sputum, saliva, urine, Cerebrospinal fluid (CSF), pleural effusion, peritoneal fluid, synovial fluid, etc., may be directly, or with additional water, added into the lysing container, by pipetting or through a sample transfer container, such as the first syringe with a relatively long needle (discussed above, not shown). When the aqueous fluid is added into lysing container, the sample fluid mixes with lysing solution, or re-hydrates the dried lysing reagents, to form a complete sample-lysing buffer mix. Preferred specimens are plasma or serum, and the preferred volumes of plasma or serum collected are in the range of 1-20 ml, more preferably at least 2 ml, even more preferably 2-10 ml, and most preferably 2-5 ml.

Other specimens in high viscosity form, or in semi-solid and solid forms, such as pus, cell suspensions and tissues, may be added into the lysing container with additional water in an amount as needed to re-hydrate the dried lysing reagents, to maintain an optimal ratio of the sample volume to the lysing solution.

The incubation in the lysing process may be accelerated at elevated temperatures (higher than ambient temperature or room temperature), by placing the lysing container into a hot-water bath or heat block. The elevated temperature for lysing may be at 50-65 C, for example, when the digestion enzyme is proteinase K. The incubation period for completion of sample lysing is typically in a range of 5 minutes to 4 hours, or more preferably in a range of between 10-30 minutes, but the invention is not limited to any particular incubation time.

Upon the completion of sample lysing after a short period of incubation, binding-extracting solution may be added into the lysing container by pipetting, pouring or by a syringe from a binding-extraction solution container (not shown).

The complete mix of aqueous sample-lysing binding-extracting fluids is transferred to the receptacle though a sample transfer container, such as a syringe 902, for extraction processing. The receptacle serves as a waste collection container, collecting all waste liquids extracting and washing processes to be performed.

In a preferred embodiment, after the extraction, the collected sample may be further processed by:

1. Washing with a wash buffer to eliminate contamination from biological samples and to clean up salts from the extraction and lysing buffer that might otherwise interfere or inhibit down-stream applications. In a preferred embodiment, a relatively large volume may be used in a single washing step. The preferred volume may be in the range of 1-10 ml, more preferably 1-5 ml, or most preferably 2-4 ml. By contrast, conventional procedures commonly use two different wash buffers and perform two wash steps, typically less than 1 ml each, because of size constraints in the column dictated by centrifuge size.

2. Rinsing with a non-water, dehydrating wash, such as with 100% ethanol (preferred) or 100% acetone, to further clean up contaminates and dehydrate the matrix. Here, too, a relatively large volume is used to dehydrate the matrix for preservation of the cNA. The preferred volume of ethanol or acetone wash liquid is in the range of 1-10 ml, more preferably at least 2 ml, or most preferably 2-6 ml. Again, by contrast, convention procedures commonly use less than 1 ml because of the size limits mentioned above. Some conventional procedures may not use an ethanol, acetone or other dehydrating wash at all.

Although shown with a tab on the filter column and a mating notch on the shipping container, any member disposed on the filter column adapted to be releasably engaged by a cooperating second member disposed on the shipping container, and capable of transmitting sufficient force to the filter column to unscrew it from its threaded connection with the receptacle cap, may be provided. Similarly, although shown with a threaded connection between the filter column and the receptacle cap, any type of interlocking connection may be used, and the respective elements of such a system may utilize any type of cooperation between the shipping container and the filter column to detach the filter column from the cap in a preferably sterile manner.

The collection system may have a three-way valve disposed between the sample transfer container and the sample collection port on the receptacle cap. Such a 3-way valve may have a first port adapted to be disposed to the receptacle cap sample connection port, a second port adapted to be connected to the transfer container, and a third port adapted to be connected to a fluid source containing a fluid, such as washing fluid containing ethanol, for treating the sample after it has been collected. A kit for collecting the nucleic acid may include a quantity of fluid needed to provide a desired level of washing, stabilization, or other type of treatment. In one embodiment, the collection container may comprise a syringe and the three way valve may comprise a check valve adapted to exclusively permit flow from the transfer container into the receptacle when a positive relative pressure exists between the sample transfer container and the receptacle, and to exclusively permit flow from the fluid source into the transfer container when a negative relative pressure exists between the sample transfer container and the fluid source. Thus, when the syringe plunger is depressed, fluid is discharged through the filter column, and when the syringe plunger is pulled out, fluid fills the syringe from the connected fluid source. Accordingly, a repeated push, pull, push motion with the syringe may discharge the original sample, pull washing fluid into the syringe, and discharge the washing fluid into the receptacle. Repeatedly pushing and pulling on the plunger may thus perform as many washing steps as may be desired.

The filter columns may be sized to fit within a sample holder (not shown) for receiving a plurality of filter columns and adapted to fit in a centrifuge for centrifuging the plurality of filter columns together at one time, such as but not limited to a size accommodated to fit a 96-well format for semi-automatic or full-automatic processing and handling.

The collection system may be sold as part of a kit comprising one or more of the materials required to perform a particular type of test, such as but not limited to the following: means for extracting a fluid sample from a patient (such as a needle and syringe for pulling blood, serum, plasma or other body fluids), lysis for breaking down cells or particles in the fluid sample, the lysing container for holding the sample plus lysing solution for a desired period of time, the sample transfer container (such as a syringe or another tube) as discussed above for mating with the receptacle as discussed above, the receptacle cap as discussed above with the filter column installed therein, any washing or other type of treatment fluid needed for preparing or stabilizing the sample for shipment, and the shipping container as discussed above.

In other embodiments, the various parts above may be sold separately. Ideally, for most types of testing, and in particular for the tuberculosis detection method referred to above, all of the parts that touch the sample or sample containing fluid from the time it is extracted from the patient until the nucleic acid is deposited on the substrate in the filter column, should be sterile or not contaminated by nucleic acid from any other sources, for example, from the operator or from environment, and not be contaminated by universally existing DNAses and RNAses, which quickly degrade nucleic acid. Various containers, syringes, and receptacles as discussed herein may be standard components well known in the laboratory/healthcare fields. The innovative receptacle cap, however, with connected filter column, is specialized for this particular collection system.

Thus, another aspect of the invention may comprise a sterile removable cap for a receptacle, the cap having an internal side for facing the internal volume of the receptacle and an external side opposite the internal side, the cap comprising a breather port communicating between the internal side and the external side, and a sample connection port communicating between the internal side and the external side, the sample connection port comprising a first interlocking component for releasably locking the sample connection port to cooperating second interlocking component, the internal side of the cap comprising a connection interface in fluid communication with the sample connection port. The removable cap described above may be sold separately, or in another embodiment, complete with a sterile filter column as discussed herein, removably attached to the connection interface of the receptacle cap.

All the parts of the system described herein may be made by any method known in the art, such as by thermoplastic injection molding. Preferred thermoplastics include polyethylene (PE), polypropylene (PP) and polyethylene terephthalate (PET), but the invention is not limited to any particular material or method of construction.

An exemplary method for using the system discussed herein may be performed as follows.

(a) collecting a volume of sample-containing fluid, which may be treated and incubated with a lysis buffer and binding buffer with chaotropic agents, salts and precipitant such as alcohol, in a container to release nucleic acids from complexes, cells or other particles in a biological sample. The crude lysate may be transferred into the sample transfer container (such as a syringe), or the collection step may take place within a suitable sample transfer container;

(b) connecting the sample transfer container to the receptacle via the sample collection port;

(c) passing the volume of sample-containing fluid from the sample transfer container through the filter column, thereby collecting nucleic acid in the crude lysed sample on the substrate and collecting a reminder in the receptacle;

(d) Washing the nucleic acid bound filter matrix in the column with washing buffers.

(e) Dehydrating (and also simultaneously further washing and desalting) the nucleic acid bound matrix by passing a volume of solvent though the column, preferred with 100% ethanol or acetone.

(f) placing the shipping container bottom portion over the filter column, engaging the filter column with the shipping container, and detaching the filter column from the receptacle cap;

(g) Temporarily sealing the shipping container by mating the shipping container top portion and shipping container bottom portion. The sealed shipping container preferably contain a pocket of moisture absorbent (desiccant), such as granular or beads silica gel.

Unlike DNA molecules, which are relatively stable, RNA molecules are more susceptible to degradation due to the ability of the 2' hydroxyl groups adjacent to the phosphodiester linkages in RNA to act as intramolecular nucleophiles in both base- and enzyme-catalyzed hydrolysis.

Washing step (d) may comprise treating the collected sample on the substrate by passing one or more volumes of treatment fluid through the filter column. For example, the treatment may comprise stabilizing the sample of nucleic acid for shipment, such as washing the sample with a washing fluid, such as a fluid comprising ethanol. In one embodiment in which the sample transfer container comprises a syringe, the method of passing the volume through the filter column may comprise manually applying pressure to a plunger of the syringe. In another embodiment in which the sample transfer container comprises a syringe, the method of passing the volume through the filter column may comprise attaching the breather port of the receptacle cap to a source of vacuum, and then applying a negative pressure across the filter column using the vacuum source. Such a method may be performed by placing the receptacle in one of the wells of the vacuum chamber shown in FIG. 5, and connecting the receptacle cap breather port to an adjacent vacuum port.

When ready for a downstream nucleic acid assay, the nucleic acid bound on the substrate in the filer column is released and eluted out from the filter column, such as by adding a small amount of elution buffer or pure water to the filter (solid matrix) to release bound nucleic acid and collecting the elute in another small container by applying pressure through the column or preferably, by centrifugation.

While not being limited to any particular use, the aforementioned collection system may be particularly useful in connection with a method for detection of Tuberculosis, as outlined herein below. The system and method may be particularly useful, however, in connection with any method that uses collection of cfNA for diagnosis, such as methods for early diagnosis of fetus genetic disorders, tumor diagnosis and infections in deep tissues, like LTBI. In summary, the system and method may be particularly useful in connection with any methods based on evaluation of NA material that contains alterations in NA information distinguishable from the host body. The system and methods described herein are particularly useful in fields in which extraction and preservation is important. Detecting low concentrations of cfNA in blood requires a relatively large volume sample (2-5-10 ml), because when reagents are added, the total volume easily reaches 20-50 ml, which is difficult volume to handle or automate using previously existing processes. RNA presents problems due to its stability. Accordingly, the method and system is particularly well suited for processes relying on detection of low concentrations of cfNA, specifically RNA, in bodily fluids.

EXAMPLES

Example 1—Construction of MOE Device

A prototype of the filter column 200 as depicted in FIG. 4 was constructed. The Mobicol filter column was supplied from Boca Scientific (FL), with a porous filter frit 214 fitted into the column. A suitable sized absorption matrix disc 212 was punched from GF/D fiber glass filter paper (Whatman, N.J.) and inserted on the top of the porous filter, then a Teflon backup ring 216 (theoringstore.com) was tightly placed on the top of absorption matrix disc, to fix the assembly. A cap with a Luer-Lock connection on its top was screwed and sealed on the filter column. The cap with assembled filter column was then screwed and sealed into an empty 50 ml plastic disposable centrifuge tube. The whole device as described above is referred to further herein as an MOE (Manually Operated Extraction) Device. The Luer-lock cap with MOE filter column underneath is screwed and sealed on a 50 ml plastic disposable centrifuge tube. Multiple MOE filter devices used in the following examples may be constructed in the same way.

Example 2—Extraction of Cell-Free Nucleic Acids from Bovine Calf Serum

In this experiment, commercially available frozen bovine calf serum (BCS) was used as an experimental model biomaterial because it is an economic, sufficient source and it contains naturally-originated bovine cell free nucleic acids. The interpretation of quantitative results of this BCS, regarding detected nucleic acid sequences, should be limited to this lot. The used BCS, HyClone™ Bovine Calf Serum (Cat. SH30072.03), was supplied by Fisher Scientific (MA). Upon arrival, the BCS was defrosted at room temperature with shaking. Once completely defrosted, the BCS was aliquoted and refrozen until use. For consistency, all aliquots of the BCS were defrosted at room temperature one time only just before use.

The cfNA in the BCS were extracted with QIAamp Circulating Nucleic Acid Kit (cat. 55114, Qiagen USA, CA), per manufacturer's instruction, as a reference. For testing the invented device and procedure under fully manual operation of the extraction and for comparison, MOE filter columns were used instead of the Qiagen Mini columns (QM column) contained in the kit. In addition, during use of the MOE filter column, the extraction and washing procedures were completed with plastic disposable Luer-lock syringes connected to the Luer-lock cap on the MOE column and operated by hand, whereas during use of the Qiagen Mini column, the liquids were transferred by pipetting and extraction-washing procedures were aided with a vacuum manifold QIAvac 24 Plus (Qiagen USA, CA), connected to an electric vacuum pump, as instructed in the kit's user manual.

Four aliquots of the defrosted BCS (2 ml of each) were added into 50 ml centrifuge tubes (labeled as QM and MOE respectively) containing lysis buffer ACL and Proteinase K and incubated at 60° C. for 30 minutes. A suitable amount of binding buffer ACB with isopropanol was added to the each tube per direction in the instruction manual. The total volume of the lysate mixture was about 8 ml.

To compare recovery using the two different extraction columns, 2 µl of a "TB-DNA" solution ($1.5 \times 10^6$ copies/µl), containing a 60 bp short double strand DNA, was spiked into one of each of the QM and MOE tubes and labeled as QM-TB and MOE-TB, respectively. The "TB-DNA" solution is prepared with a PCR amplicon of IS6110 gene fragment, from genome *Mycobacterium tuberculosis* stain h37Rv. The dsDNA was spiked into the BCS as foreign DNA control (exogenous to the host). Thus, the 4 tubes are labeled as QM, QM+TB, MOE and MOE+TB respectively.

The ACB-lysate mixture in the QM tube was transferred to an extension tube, connecting the QM column to the vacuum manifold. Extraction and washing procedures using isopropanol-containing ACW1 and ACW2 wash buffers were completed by pipetting and vacuuming.

The ACB-lysate mixture in the MOE tube was drawn into a 20 ml Luer-lock syringe attached with a long needle. Then, the needle was removed and the syringe was screwed firmly onto the Luer-lock connector of the cap 101 on a 50 ml centrifuge tube (400). The lysate mixture in the syringe was pushed through the binding matrix in the MOE filter column by hand pressure. The wash buffers ACW1 and ACW2 were also transferred into and passed through the MOE filter column using smaller syringes. The volume of a syringe used in this invention should be large enough so that in addition to the liquid phase occupied in a syringe, a sufficient air phase should be reserved to purge out liquid residues remaining in the filter matrix and in the column as much as possible.

The absorbed cNA fragments in both columns were eluted in 60 μl of buffer AVE by high-speed centrifugation (15,000 g). The elutes were used immediately, or kept frozen.

A portion of the eluates containing extracted cell-free mRNA were reversely transcribed with M-MLV Reverse Transcriptase (cat. M170, Promega, Wis.) and random primers to cDNA, according to manufacturer's protocol. Quantification of the cfDNA and cf-mRNA was determined by Quantitative Real-Time PCR with SIBO™-SYBR qPCR mixture kit (commercially available from Occam Biolabs, DE). Other commercially available SYBR qPCR kits, such as SYBR® Premix DimerEraser™ (Perfect Real Time, Takara-Clontech, CA), Power SYBR® Green PCR Master Mix (Life Technologies, CA) and iQ™ SYBR® Green Supermix 2× Real-Time PCR Mix (Bio-Rad, CA) may also be used for this purpose. The primer pairs used for the qPCR assay are listed in Table 1. Those primers, targeting an exogenous sequence of *M. tuberculosis* gene IS6110 and an endogenous sequence of B. B. Taurus mitochondrial gene Nd2, are designed specifically to amplify short DNA sequences. In the RT-qPCR assay, the forward primers and reverse primers, targeting different sequences of commonly used housekeeping genes B2M (beta-2-microglobulin), are designed to be complementary to different exons crossing large size introns; thus, only short cDNA which are reversely transcribed from mRNA, but not contaminated genomic DNA, are amplified and detected.

TABLE 1

Primers used in detection of cNA in bovine calf serum.

| PCR primer ID | | Sequence (5'-) | Gene | In Exon | Intron (bp) | Amplicon (bp) |
|---|---|---|---|---|---|---|
| Organism | | *B. Taurus* | | | | |
| BB2m11 | F | CCTTGGTCCTTCTCGGGCTG (SEQ ID NO: 1) | B2m | 1 | 5735 | 98 |
| | R | TTCCATCTTCTGGTGGGTGTC (SEQ ID NO: 2) | | 2 | | |
| BB2m22 | F | CTTCGTGGCCTTGGTCCTTC (SEQ ID NO: 3) | B2m | 1 | 5735 | 100 |
| | R | TTCTGGTGGGTGTCTTGAGT (SEQ ID NO: 4) | | 2 | | |
| BB2m33 | F | CTTCGTGGCCTTGGTCCTTCTC (SEQ ID NO: 5) | B2m | 1 | 5735 | 143 |
| | R | GATGGAACCCATACACATAGCA (SEQ ID NO: 6) | | 2 | | |
| BB2m44 | F | CGAGTGAAACACGTTACTTTGGA (SEQ ID NO: 7) | B2m | 2 | 522 | 71 |
| | R | GATGGTGCTGCTTACAGGTCTC (SEQ ID NO: 8) | | 3 | | |
| BNd211 | F | TCCCAGAAGTAACACAGGGCA (SEQ ID NO: 9) | Nad2 | mt DNA | NA | 48 |
| | R | GTAGGATAAGGCCTGAGGATAG (SEQ ID NO: 10) | | | | |
| Organism | | *M. tuberculosis* | | | | |
| IS611065 | F | GGTCAGCACGATTCGGAG (SEQ ID NO: 11) | IS6110 | | NA | 60 |
| | R | GCCAACACCAAGTAGACGG (SEQ ID NO: 12) | | | | |

TABLE 2

Results summary of Quantitative PCR for cfDNA and cfRNA

| Primer ID | cfNA species | Amplicon (bp) | Melt Temp. (Tm C.) | Ct QM | Ct MOE | Ct QM + TB | Ct MOE + TB |
|---|---|---|---|---|---|---|---|
| BB2m11 | mRNA | 98 | 84.1 | 28.58 | 28.13 | 28.95 | 27.79 |
| BB2m22 | mRNA | 100 | 85.1 | 28.06 | 27.93 | 27.51 | 27.68 |
| BB2m33 | mRNA | 143 | 84.8 | 28.61 | 27.63 | 27.97 | 28.21 |
| BB2m44 | mRNA | 71 | 80.0 | 24.43 | 24.80 | 25.05 | 24.17 |

TABLE 2-continued Results summary of Quantitative PCR for cfDNA and cfRNA

| Primer ID | cfNA species | Amplicon (bp) | Melt Temp. (Tm C.) | Ct QM | Ct MOE | Ct QM + TB | Ct MOE + TB |
|---|---|---|---|---|---|---|---|
| BNd211 | DNA | 48 | 77.6 | 27.16 | 28.09 | 27.77 | 28.56 |
| IS611065 | DNA* | 60 | 83.2 | ND | ND | 22.08 | 22.26 |

*Spiked exogenous DNA
ND: NotDetectable

The results show that, when the same buffers, i.e. ACL, ACB, ACW1, ACW2 and AVE of QIAamp circulating NA kit, are used, both the MOE filter column using manually syringe-operated procedures in accordance with an embodiment of the present invention, and the Qiagen Mini column processed using a vacuum pump, have comparable extraction efficiency of cfNDA and cfRNA. The results also show the possibility of using mRNA fragments in peripheral circulation as an endogenous reference standard and quality control for a biological specimen.

Example 3

In this example, only the MOE filter column was used with following buffers and protocol:
Buffers:
Lysis Buffer (LB): containing guanidine thiocyanate (GITC), 4 M, Triton X-100 8%, Qiagen Proteinase K (cat. 19131, Qiagen, CA), 100 µl/ml LB.
Binding Buffer (BB): containing 3 M GITC, 40% isopropanol (IPA, final concentration), mixing very well.
Washing Buffer (WB): containing 10 mM Tris, 2 mM EDTA, 10 mM NaCl, 70% ethanol, pH 7.0.
Elution Buffer: Qiagen Buffer AVE (included in QIAamp Circulating Nucleic Acid kit).
Protocol:
 1. Lysis: Draw 2 ml of defrosted BCS by a 10 ml syringe with a long needle, into a 50 ml plastic centrifuge tube containing 2 ml LB, mix well by vortexing, incubate in 60° C. heat block for 30 minutes. Cool down at room temperature.
 2. Binding: Draw 10 ml of BB into the sample lysate tube, mix it by vortexing, keep it in room temperature for 10 minutes.
 3. Binding and Extraction: Draw all the content in the 50 ml lysate tube into a 20-30 ml Luer-lock syringe with a long needle, continuing until drawing about 5 ml air into the syringe, screw the Luer-lock syringe onto the female Luer-lock connector on the cap of assembled MOE device 400, which is seated in a rack firmly. Press the syringe plunger down until all liquid and air in the syringe pass through the filter column. The waste is collected in the 50 ml tube of the MOE device. This procedure may take 1-2 minutes. Unscrew the 20 ml syringe.
 4. Draw 4 ml of WB into a 10 ml Luer-lock syringe, press the plunger to allow WB pass through the column. Unscrew the 10 ml syringe.
 5. Draw 4 ml of 100% Ethanol into a 10 ml Luer-lock syringe, press the plunger to allow the ethanol pass through the column.
 6. Unscrew the cap of MOE device and detach the filter column from the cap. Insert the column into a 1.5-2 ml RNase-, DNase-free micro-centrifuge tube, Air-dry ethanol residue in the column completely.
 7. Add 100 µl of elution Buffer AVE directly onto the absorption matrix in the filter column, screw a cap on the filter column to prevent contamination in handling. Wait for 10-30 minutes to rehydrate and release the bound NA from the absorption matrix.
 8. Centrifuge the micro tube with the inserted column inside it at 15,000-20,000 G for 3 minutes. Collect the elute for down-stream applications or store in −20 to −80 C.

In this experiment, 2 ml of LB was added into 6 of 50 ml centrifuge tubes and followed by 2 ml of BCS. In addition, 2 µl of 10-fold diluted "TB-DNA" solution ($1.5 \times 10^5$ copies/µl) was spiked into each of the lysis tubes. The following procedure was accomplished according to the above protocol up to step 6.

After step 6, the 6 MOE columns were divided into 3 sets of identical duplicates (A and B) and labeled as MOE-0 wk, MOE-2 wk and MOE-4 wk for each set, indicating further treatment for none, 2 weeks and 4 weeks, respectively.

Further treatment was as follows: the set labeled MOE-0 wk was immediately subjected to step 7 of the above procedure; sets labeled MOE-2 wk and MOE-4 wk were kept in new 50 ml centrifuge tubes, with a packet of silica gel desiccant Minipax® absorbent packets (cat. Z163554, 0.5 g/packet, Sigma-Aldrich, MO). The 50 ml tubes were closed tightly and wrapped with pieces of Parafilm (VWR, PA) to ensure complete sealing. The tubes sealed with the filter columns inside were exposed to room temperature for 2 weeks (MOE-2 wk) and 4 weeks (MOE-4 wk), respectively. At the end of exposure, the two sets were opened and the filter columns were processed via step 7 of the above procedure.

After step 8, all elutes were assayed with qPCR and RT-qPCR, as demonstrated in Example 2. The results are shown in Table 3.

By comparing the Ct values of the samples eluted from the columns immediately to the samples eluted after exposure to room temperature for 2 weeks and 4 weeks, it was surprisingly found that in all of the different species of cfNA fragments examined by qPCR and RT-qPCR, the quantity and therefore the integrity (amplifiable) were almost identical. By contrast, when the filter columns after step 7 were exposed to normal humility and room temperature for a few days, the absorbed cfNA, in particular RNA species, became degraded and not be amplifiable (data not shown).

The surprise discovery means that after the extraction, the absorbed cfNA, in particular, vulnerable cfRNA on the filter matrix, can be stabilized and well preserved in room temperature. Large volume of ethanol (4 ml in this case) flushing the porous absorption matrix, and furthermore, keeping the absorbed NA in dehydrated status in a closed environment with desiccant, effectively protect RNA from degradation. The simple, economical treatment for absorbed NA provides an easy way to handle, store and transport biological specimens.

TABLE 3

| Primer ID | cfNA species | Amplicon (bp) | Melt Temp. (Tm C.) | Sample Group | Ct In Room Temperature for 0 wk | 2 wk | 4 wk |
|---|---|---|---|---|---|---|---|
| BB2m11 | mRNA | 98 | 84.1 | A | 25.23 | 25.38 | 26.24 |
|  |  |  |  | B | 25.51 | 26.61 | 25.75 |
| BB2m22 | mRNA | 100 | 85.1 | A | 26.56 | 25.32 | 26.68 |
|  |  |  |  | B | 26.39 | 27.2 | 25.89 |
| BB2m33 | mRNA | 143 | 84.8 | A | 28.15 | 27.49 | 27.84 |
|  |  |  |  | B | 27.22 | 27.83 | 27.81 |
| BB2m44 | mRNA | 71 | 80.0 | A | 24.21 | 26.01 | 25.70 |
|  |  |  |  | B | 24.26 | 26.26 | 24.96 |

TABLE 3-continued

| Primer ID | cfNA species | Amplicon (bp) | Melt Temp. (Tm C.) | Sample Group | Ct In Room Temperature for 0 wk | 2 wk | 4 wk |
|---|---|---|---|---|---|---|---|
| BNd211 | DNA | 48 | 77.6 | A | 27.08 | 27.34 | 26.27 |
|  |  |  |  | B | 27.24 | 27.87 | 27.09 |
| IS611065 | DNA* | 60 | 83.2 | A | 26.78 | 26.24 | 26.47 |
|  |  |  |  | B | 26.26 | 25.82 | 26.32 |

Example 4—Detection of Pathogen-Specific Nucleic Sequence in Human Peripheral Blood Fresh human peripheral blood was drawn from two adult subjects (a Health control and a latent tuberculosis infection suspect, HC and LTBI respectively). The LTBI subject is defined as PPD skin test positive, who lives in TB low-burden country for 25 years, but has recent TB contact history in a TB high-burden country in the last two years. During the last two years, the subject was tested by CT X-ray examination three times, sputum smear test four times and TB culture three times. All of those tests turned out negative but the tuberculin skin test (PPD) converted from negative to positive (1.8 cm). The subject had no symptoms related to tuberculosis. The subject was presumptively defined as LTBI by a medical professional. It is well known there some major barricades in LTBI diagnostics; in particular, there are no means to obtain direct evidence for the bacterial infection in the body using current technology. No other additional test for LTBI diagnosis has been used for this case.

The plasma was separated from whole blood by centrifugation (2000 g, 10 minutes). cNA were extracted as the same procedure demonstrated in Example 3. Human endogenous cNA fragments in the plasma were detected and quantified through qPCR and RT-qPCR, through 3 primer pairs of commonly used housekeeping genes B2M (beta-2-microglobulin) and PPIA (peptidylprolyl isomerase A, or cyclophilin A), and ND4 (NADH dehydrogenase subunit 4, in mitochondrial NDA) as well as TB IS6110-65, for detection of TB specific DNA fragments in peripheral blood from the suspected LTBI subject.

The primers used in the Example 4 are shown in Table 4.

TABLE 4

| PCR primer ID |  | Sequence (5'-) | Gene | In Exon | Intron (bp) | Amplicon (bp) |
|---|---|---|---|---|---|---|
| HB2M11 | F | CGCGCTACTCTCTCTTTCTGG (SEQ ID NO: 13) | B2M | 1 | 3809 | 146 |
|  | R | AGTCAACTTCAATGTCGGATGG (SEQ ID NO: 14) |  | 2 |  |  |
| HPPIA11 | F | CCAACACAAATGGTTCCCAG (SEQ ID NO: 15) | PPIA | 4 | 1412 | 180 |
|  | R | CGAGTTGTCCACAGTCAGCA (SEQ ID NO: 16) |  | 5 |  |  |
| HND411 | F | GCCTACGACAAACAGACCTAAA (SEQ ID NO: 17) | ND4 | mt DNA | NA | 45 |
|  | R | TTGAAGAGTATGCAATGAGCGA (SEQ ID NO: 18) |  |  |  |  |
| IS611065 | F | GGTCAGCACGATTCGGAG (SEQ ID NO: 11) | IS6110 |  | NA | 60 |
|  | R | GCCAACACCAAGTAGACGG (SEQ ID NO: 12) |  |  |  |  |

Figure 8A:
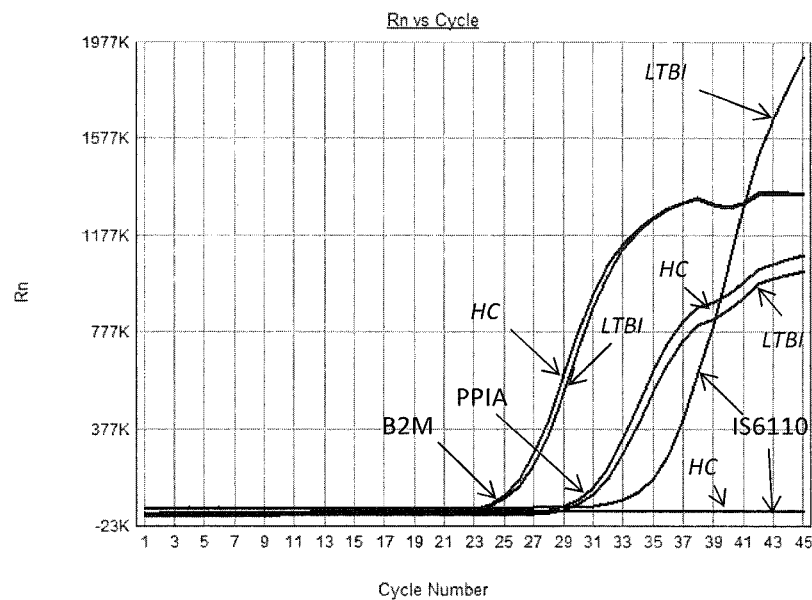
FIG. 8A shows RT-qPCR and qPCR amplification curves for fragments of human gene B2M, PPIA and a TB gene IS6110, by primer pairs HB2M11, HPPIA11, and IS6110, for extracts from human plasma of donors of HC and LTBI, respectively.
Figure 8B:
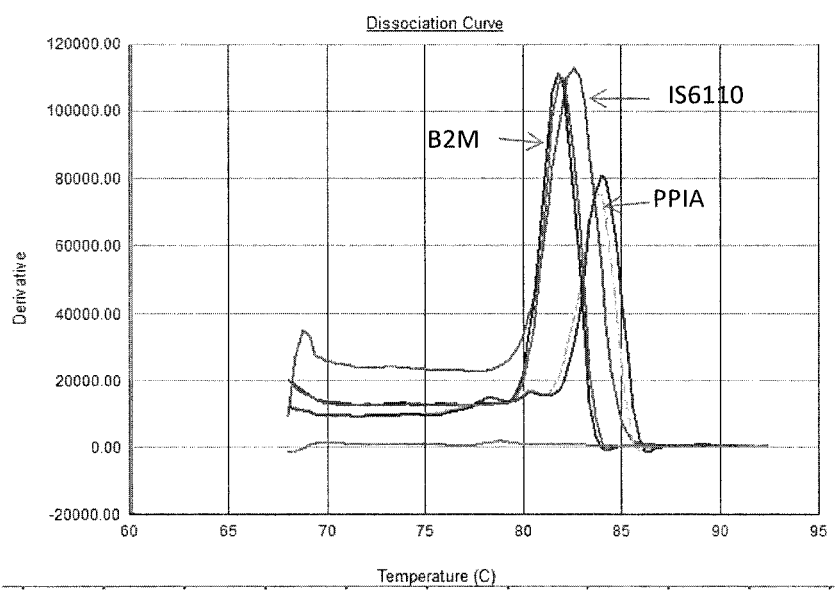
FIG. 8B shows amplicon melting curves for fragments of human gene B2M, PPIA and a TB gene IS6110, by primer pairs HB2M11, HPPIA11, and IS6110, for extracts from human plasma of donors of HC and LTBI, respectively.

The results are shown in Table 5 and in FIG. 8.

TABLE 5

| Primer ID | cfNA species | Amplicon (bp) | Melt Temp. (Tm C.) | Ct HC* | LTBI** | Ref. FIG |
|---|---|---|---|---|---|---|
| HB2M11 | human mRNA | 146 | 81.9 | 22.90 | 23.29 | FIG. 8 B2M |
| HPPIA11 | human mRNA | 180 | 84.0 | 28.29 | 28.61 | FIG. 8 PPIA |
| HND411 | human mtDNA | 45 | 75.5 | 20.99 | 22.32 | Not shown |
| IS611065 | TB DNA | 60 | 82.6 | ND | 31.47 | FIG. 8 IS6110 |

HC*: health Control

LTBI**: Latent TB Infection

ND: Not detectable

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for collecting a sample of nucleic acid, the system comprising:
   a receptacle defining an internal volume;
   a removable cap for the receptacle, the cap having an internal side facing the internal volume of the receptacle and an external side facing away from the internal volume, the cap comprising a breather port communicating between the internal side and the external side and a sample connection port communicating between the internal side and the external side, the sample connection port comprising a first interlocking component for releasably locking the sample connection port to a cooperating second interlocking component, the internal side of the cap comprising a connection interface in fluid communication with the sample connection port;
   a filter column adapted to be removably attached to the connection interface of the receptacle cap, the filter column having an open first end, an open second end, and an internal passage therebetween containing a substrate for collecting the nucleic acid;
   a sample collection container comprising the second interlocking component adapted to connect to the first interlocking component of the sample collection port in the receptacle cap;
   a shipping container having an open end and defining a volume adapted to contain the filter column, the shipping container adapted to releasably engage the filter column for detaching it from the connection interface of the receptacle cap, the shipping container further comprising a removable lid for temporarily sealing the filter column within the shipping container.

2. The collection system of claim 1, wherein the filter column substrate comprises a filter, a frit upstream of the filter, and a retaining ring downstream of the filter.

3. The collection system of claim 1, wherein the sample connection port protrudes from the external side of the cap.

4. The collection system of claim 3, wherein the sample connection port first interlocking component comprises one end of a Luer lock fitting.

5. The collection system of claim 1, wherein the breather port protrudes from the external side of the cap.

6. The collection system of claim 1 further comprising a vacuum chamber, the vacuum chamber having an internal portion adapted to be connected to a source of vacuum, an external portion having one or more wells, each well adapted to receive one of the receptacles, and one or more vacuum connection ports in communication with the internal portion of the chamber and adapted to be connected to the breather port of the receptacle via a flexible conduit.

7. The collection system of claim 1, further comprising a desiccant in the shipping container.

8. The collection system of claim 1, wherein the filter column comprises a first component of a threaded interface and the receptacle cap comprises a second component of the threaded interface.

9. The collection system of claim 8 wherein the filter column further comprises a first member disposed on an external surface thereof adapted to be releasably engaged by a cooperating second member disposed on an internal surface of the shipping container, the second member adapted to transmit force to the first member when a torsional force is applied to the filter column in a direction for unscrewing the filter column from its threaded connection with the receptacle cap.

10. The collection system of claim 9, wherein the first and second members each comprises tabs.

11. The collection system of claim 1, further comprising a three-way port having a first port adapted to be disposed to the receptacle cap sample connection port, a second port adapted to be connected to the collection container, and a third port adapted to be connected to a fluid source containing a fluid for treating the sample after it has been collected.

12. The collection system of claim 11, further comprising one or more containers of fluid adapted to be connected to the third port.

13. The collection system of claim 11, wherein the collection container comprises a syringe and the three way port comprises a check valve adapted to exclusively permit flow from the collection container into the receptacle when a positive relative pressure exists between the sample collection container and the receptacle, and to exclusively permit flow from the fluid source into the collection container when a negative relative pressure exists between the sample collection container and the fluid source.

14. The collection system of claim 12, wherein the fluid comprises a fluid for washing the sample.

15. The collection system of claim 14, wherein the fluid comprises ethanol.

16. The collection system of claim 1 further comprising a sample holder for receiving a plurality of filter columns and adapted to fit in a centrifuge for centrifuging the plurality of filter columns.

17. A method for collecting a sample of nucleic acid, the method comprising the steps of:
 (a) providing a collection system comprising
  i) receptacle defining an internal volume;
  ii) a removable cap for the receptacle, the cap having an internal side facing the internal volume of the receptacle and an external side facing away from the internal volume, the cap comprising a breather port communicating between the internal side and the external side and a sample connection port communicating between the internal side and the external side, the sample connection port comprising first means for releasably locking the sample connection port to cooperating second means, the internal side of the cap comprising a connection interface in fluid communication with the sample connection port;
  iii) a filter column removably attached to the connection interface of the receptacle cap, the filter column having an open first end, an open second end, and an internal passage therebetween containing a substrate for collecting the nucleic acid;
  iv) a sample collection container comprising the second means adapted to connect to the first means of the sample collection port receptacle cap;
  v) a shipping container having an open end and defining a volume adapted to contain the filter column, the shipping container adapted to releasably engage the filter column for detaching it from the connection interface of the receptacle cap, the shipping container further comprising a removable lid for temporarily sealing the filter column within the shipping container;
 (b) collecting a volume of sample-containing fluid in the sample collection container;
 (c) connecting the sample collection container to the receptacle via the sample collection port;
 (d) passing the volume of sample-containing fluid from the sample collection container through the filter column, thereby collecting the sample on the substrate and collecting a reminder in the receptacle;
 (e) placing the shipping container open end over the filter column, engaging the filter column with the shipping container, and detaching the filter column from the receptacle cap;
 (f) temporarily sealing the shipping container with the removable lid.

18. The method claim 17, wherein the sample-containing fluid comprises a lysate comprising an extract of bodily fluid collected from a patient.

19. The method of claim 17, wherein the sample collection container comprises a syringe and the method of passing the volume through the filter column comprises manually applying pressure to a plunger of the syringe.

20. The method of claim 17, wherein the sample collection container comprises a syringe, and the method of passing the volume through the filter column comprises attaching the breather port of the receptacle cap to a source of vacuum, and then applying a negative pressure across the filter column using the vacuum source.

21. The method of claim 17, further comprising treating the collected sample on the substrate after step (d) by passing one or more volumes of fluid through the filter column before performing step (e).

22. The method of claim 21, wherein the treatment fluid comprises a washing fluid.

23. The method of claim 22, wherein the washing fluid comprises 100% ethanol or 100% acetone.

24. The method of claim 23, wherein the washing fluid comprises 1-10 ml of 100% ethanol.

25. The method of claim 24, wherein the washing fluid comprises at least 2 ml of 100% ethanol.

26. The method of claim 25, wherein the washing fluid comprises 2-6 ml of 100% ethanol.

27. The method of claim 23, further comprising placing a desiccant in the shipping container.

28. The method of claim 27, further comprising transporting the shipping container under ambient, non-climate-controlled conditions.

29. The method of claim 28, further comprising further processing the nucleic acid after a period of time up to 4 weeks after completion of step (f).

30. The method of claim 29, wherein the further processing comprises processing of the nucleic acid for detection of a disease.

31. The method of claim 30, wherein the disease is tuberculosis.

32. The method of claim 31, wherein the processing is for detection of latent tuberculosis.

33. The method of claim 17, wherein the sample-containing fluid comprises plasma or serum.

34. The method of claim 33, wherein the volume of sample-containing fluid collected is in a range of 1-20 ml.

35. The method of claim 34, wherein the volume of sample-containing fluid collected is at least 2 ml.

36. The method of claim 35, wherein the volume of sample-containing fluid collected is in a range of 2-10 ml.

37. The method of claim 36, wherein the volume of sample-containing fluid collected is in a range of 2-5 ml.

* * * * *